United States Patent
Cho et al.

(10) Patent No.: US 7,396,589 B2
(45) Date of Patent: Jul. 8, 2008

(54) CORE-SHELL MAGNETIC NANOPARTICLES COMPRISING AN INNER-TRANSITION ELEMENT

(75) Inventors: Hui-Ju Cho, Changhua County (TW); Sheng-Ming Shih, Taipei (TW); Yuh-Jiuan Achuan Lin, Taipei County (TW); Hong-Dun Lin, Taipei (TW); Kang-Ping Lin, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/687,697

(22) Filed: Mar. 19, 2007

(65) Prior Publication Data

US 2007/0166232 A1 Jul. 19, 2007

Related U.S. Application Data (63) Continuation-in-part of application No. 11/336,347, filed on Jan. 20, 2006, which is a continuation-in-part of application No. 10/741,238, filed on Dec. 19, 2003, now abandoned.

(30) Foreign Application Priority Data

Jul. 31, 2003 (TW) .............................. 92120948 A (51) Int. Cl.
  *B32B 5/16* (2006.01)
(52) U.S. Cl. ....................... 428/403; 977/773; 977/777; 977/904

(58) Field of Classification Search ................. 428/403; 977/773, 777, 904
See application file for complete search history.

(56) References Cited

U.S. PATENT DOCUMENTS

| | | | | |
|---|---|---|---|---|
| 4,970,124 | A * | 11/1990 | Oltean et al. ................. 428/570 |
| 5,427,767 | A * | 6/1995 | Kresse et al. .............. 424/9.32 |
| 6,203,768 | B1 * | 3/2001 | McCormick et al. ........... 423/1 |
| 6,530,944 | B2 | 3/2003 | West et al. |
| 6,689,338 | B2 | 2/2004 | Kotov |

OTHER PUBLICATIONS

Haik, Magnetic Nanoparticles for Self-Controlled Hyperthermia, Apr. 2006.*
"Lanthanide and boron oxide-coated α-Fe particles" Feiyue Li, et al., J. Appl. Phys. 79 (8), Apr. 15, 1996, pp. 4869-4871.
"Synthesis and magnetic properties of CoFe2O4 spinel ferrite nanoparticles doped with lanthanide ions" Myrtil Kahn, et al., Appl. Phys. 78 (23), Jun. 4, 2001, pp. 3651-3653.

(Continued)

*Primary Examiner*—H. T Le
(74) *Attorney, Agent, or Firm*—Thomas, Kayden, Horstemeyer & Risley (57) ABSTRACT

Magnetic nanoparticles are applicable in imaging, diagnosis, therapy, and biomaterial separation. The magnetic nanoparticles comprise a core represented as $Fe_xM^a_vZ_y$ and a shell of an inner-transition element $M^b$ or the compound thereof, wherein $M^a$ is an inner-transition element, Z is an element of the group VIa, x is greater or equal to 0, and v, y are positive numbers. The surface of the shell is optionally modified by liposome, polymer, aliphatic compound, aromatic compound or combinations thereof.

27 Claims, 13 Drawing Sheets

OTHER PUBLICATIONS

Kahn and Zhang, "Synthesis and magnetic properties of CoFe2O4 spinel ferrite nanoparticles doped with lanthanide ions", Appl. Phys. Lett, vol. 78, No. 23, Jun. 4, 2001, 3651-3653.*

Li et al., "Lanthanide and boron oxide-coated alpha-Fe particles", J. Appl. Phys. 79 (8), Apr. 15, 1996, 4869-4871.*

* cited by examiner

FIG. 1

$Gd^{3+}/(Gd^{3+}+Fe^{2+}+Fe^{3+})= 0$ mole%

FIG. 2a

$Gd^{3+}/(Gd^{3+}+Fe^{2+}+Fe^{3+})= 2.46$ mole%

FIG. 2b $Gd^{3+}/(Gd^{3+}+Fe^{2+}+Fe^{3+})= 3.33$ mole%

FIG. 2c $Gd^{3+}/(Gd^{3+}+Fe^{2+}+Fe^{3+})= 6.67$ mole%

CORE-SHELL MAGNETIC NANOPARTICLES COMPRISING AN INNER-TRANSITION ELEMENT

CROSS REFERENCE TO RELATED APPLICATIONS

This application is a continuation-in-part (CIP) of U.S. application Ser. No. 11/336,347, filed Jan. 20, 2006 (which is incorporated herein by reference), which is a CIP of U.S. application Ser. No. 10/741,238 filed Dec. 19, 2003 (which is incorporated herein by reference), which claimed the benefit of Taiwanese Application No. 92120948, filed Jul. 31, 2003.

BACKGROUND OF THE INVENTION

1. Field of the Invention

The present invention relates to magnetic nanoparticles applicable in imaging, diagnosis, therapy and biomaterial separation, and more particularly to magnetic nanoparticles suitable for use as contrast agents in Magnetic Resonance Imaging and a fabrication method thereof.

2. Description of the Related Art

In the biotechnology field, magnetic nanoparticles are applicable in imaging, diagnosis, therapy, biomaterial separation and so on. It is used, for example, in imaging as a contrast agent or a tracer to enhance the imaging contrast or to trace the presence of a certain disease. Furthermore, magnetic nanoparticles are also applicable in drug delivery and cancer therapy.

Currently, a number of image analysis techniques such as Computer Topography (CT), Magnetic Resonance Imaging (MRI), and ultrasound (US) are applied in disease diagnosis. The popular analysis technique of computer topography employs an X-ray to image for example, a human body by X-ray diffraction of various tissues with various densities. In addition, a contrast agent may be added during analysis to enhance the contrast among different tissues or organs. However, the radiation of X-rays may bring undesired side effects, thus Magnetic Resonance Imaging (MRI) has been provided as an alternative analysis technique.

Magnetic resonance imaging is capable of showing selectively image several different characteristics of tissues. The level of tissue magnetization at specific signal recording times during the MR imaging cycle generally determines the brightness of a particular tissue in the MRI images. Contrast is produced when tissues do not have the same level of magnetization. There are three primary magnetic characteristics of tissue that are the source of image contrast. Two of these are associated with the longitudinal magnetization. They are proton density and T1, the longitudinal relaxation time. The third characteristic is associated with the transverse magnetization. It is T2, the transverse relaxation time.

Diagnosis of brain disorders has been markedly improved by using MRI, which can delineate detailed anatomic structures with excellent tissue contrast on T1, T2, and proton density-weighted images; however, the inherent tissue characteristics do not always produce adequate contrast for some clinical applications. The administer materials that will alter the magnetic characteristics within specific tissues or anatomical regions, and can disclose abnormal enhancement after intravenous administration of contrast agents due to brain-blood-barrier (BBB) disruption. Advanced MR imaging technique, which can detect in vivo physiological changes in human brain, such as water diffusion, blood volume and blood flow have been implemented in clinical MR scanners.

Certain materials are susceptible to magnetic field and become magnetized when located in field. The orbital electrons in the atom rather than magnetic properties of the nucleus determine the susceptibility of a material. Contrast agents used in MRI are generally based on susceptibility effects. Using dynamic susceptibility contrast technique takes the advantage of T2 signal changes during the first-pass of a bolus of contrast agents. Hemodynamic parameters can then be calculated in terms of cerebral blood volume (CBV), cerebral blood flow (CBF) and mean transit time (MTT) for diagnosis in clinical.

MRI provides a non-invasive diagnosis. An MRI with contrast agent enhancement increases sensitivity and specificity of imaging in many cases particularly when relaxation times among different tissues are similar.

MRI contrast agents can be classified differently according to their magnetic properties (paramagnetic, ferromagnetic or superparamagnetic). However, current commercial MRI contrast agents employing magnetic nanoparticles have poor specificity and their contrast enhancement could be improved.

U.S. Pat. No. 5,427,767 discloses iron oxide doped with an isotope, such as, $^{155}$Gd, $^{156}$Gd, or $^{157}$Gd. Pure isotopes, however, are much higher in cost than a natural isotope mixture. Further, the doping ratio and its effect on improving magnetization or transverse relaxivity (r2) are not discussed. The core/shell structure of the disclosed is a metal core coated by an organic molecular shell.

J. Appl. Phys. Vol. 79, No. 8, page 4869-4871 discloses lanthanide and boron oxide-coated α-Fe particles. The shell of the particles comprises inner-transition metal, and further comprises boron oxide as $B_2O_3$.

Similar to U.S. Pat. No. 5,427,767, Appl. Phys. Lett. Vol. 78, No. 23, page 3651-3653 discloses a $CoFe_2O_4$ nanoparticle doped with lanthanide ions. The $CoFe_2O_4$ nanoparticles are only doped with lanthanide ions, and the lanthanide ions do not form a shell coating on the $CoFe_2O_4$ nanoparticles.

BRIEF SUMMARY OF THE INVENTION

The invention provides magnetic nanoparticles comprising a core represented as $Fe_xM^a_vZ_y$ and a shell of an inner-transition element $M^b$ or the compound thereof, wherein $M^a$ is an inner-transition element, Z is an element of the group VIa, x is greater or equal to 0, and v, y are positive numbers. The magnetic nanoparticles can be selectively modified by at least one molecule (such as liposome, polymer, aliphatic compound or aromatic compound), or further react with at least one substance having specificity (such as an antibody, protein, peptide, enzyme, carbohydrate, glycoprotein, nucleotide or lipid) to form contrast agents or tracers with specificity. $M^a$ and $M^b$ can be same or different inner-transition element. The magnetic nanoparticles can be applicable in imaging, diagnosis, therapy, and biomaterial separation. For example, the magnetic nanoparticles having specificity can perform a specific therapy such as killing cancer cells without harming healthy cells after entering the patient by heat transferred from the external magnetic field.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

EXAMPLE 1

In Example 1, a magnetic nanoparticle of iron oxide comprising an inner-transition element of Gadolinium is given as an example, while the inner-transition element of the invention is not limited to this, for example, the inner-transition element can be any of the lanthanides or the actinides, and the compound of the inner-transition element can be an oxide, sulfide, selenide, telluride, or polonide of the inner-transition element. Also, the amount of the inner-transition element in the magnetic nanoparticle is not limited.

Preparation of Gd-Including Iron Oxide Nanoparticles

In Example 1, Gd-including iron oxide nanoparticles were utilized as an MRI contrast agent. First, a reaction flask was charged with $FeCl_2$ powders (0.0069 moles), $FeCl_3$ powders (0.0138 moles) and deionized (Dl) water (30 ml). $FeCl_3$ powders were replaced by $GdCl_3$ in various ratios in other examples. NaOH with a concentration of 5M was added to control the pH value of the mixture. The mixture was subjected to continuous stirring during the reaction till the mixture became basic solution (the pH value approached about 11.5). Afterward, the temperature of the mixture was raised to and remained at 65° C. for 10 minutes. After black precipitates were formed, they were washed by Dl water and adjusted to acidic state by glacial acetic acid. Finally, $H_2O_2$ (10 vol %) was gradually added until the end of the gaseous reaction, and was followed by a Dl water wash.

Characterization of Gd-Including Iron Oxide Nanoparticles

1. Transmission Electron Microscope (TEM)

The magnetic nanoparticles were then observed by TEM (JOEL, 100CX II). FIGS. 2a-2d respectively show the magnetic nanoparticles with an initial $Gd^{3+}/(Gd^{3+}+Fe^{2+}+Fe^{3+})$ mixing ratio of 0, 2.46, 3.33 and 6.67 mol %. In these cases, their average diameters are about 8.2±1.6 nm, 14.6±2.7 nm, 19.6±3.2 nm and 22.1±3.5 nm, respectively.

2. X-Ray Diffraction (XRD)

Figure 1:
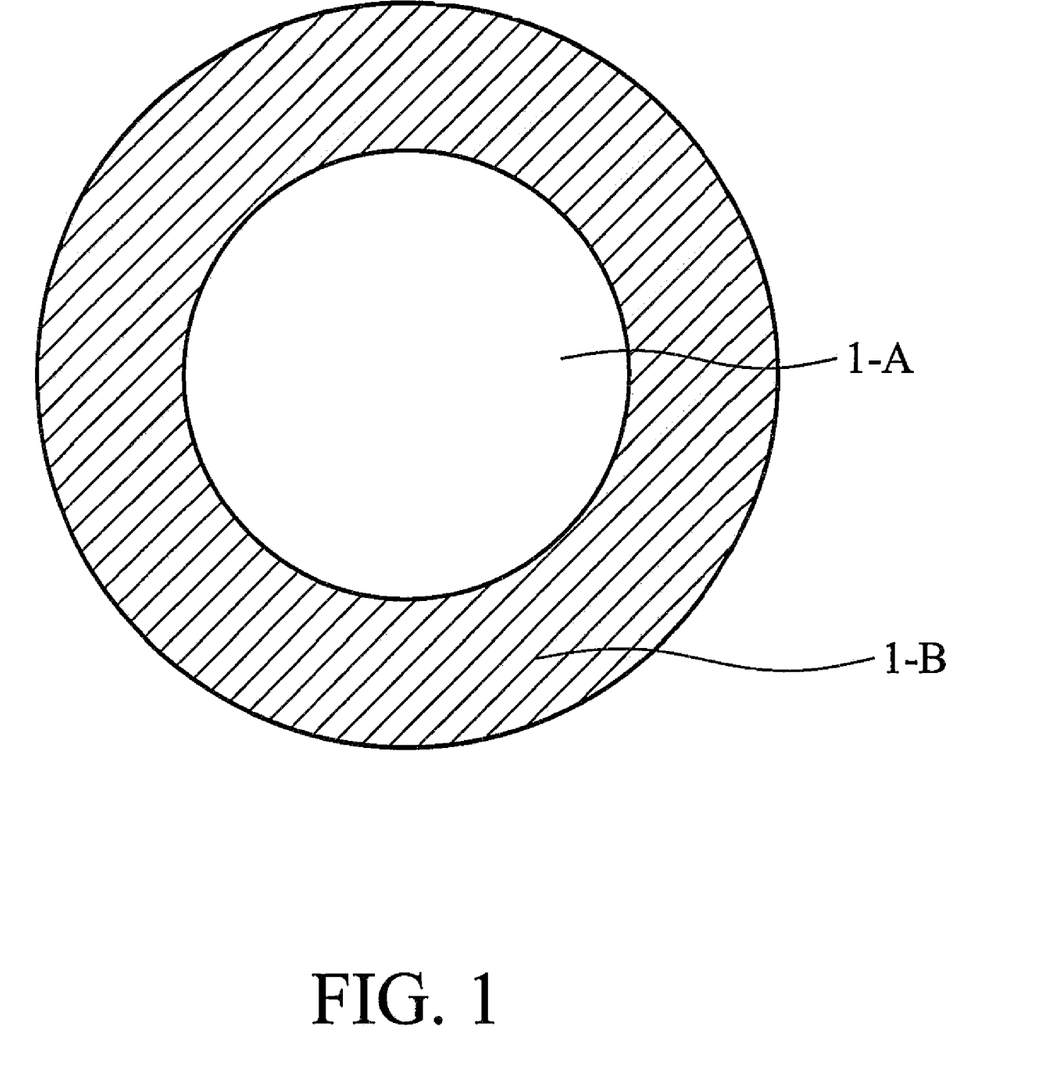
FIG. 1 illustrates the core-shell structure of a magnetic nanoparticle of the invention.
Figure 2A:
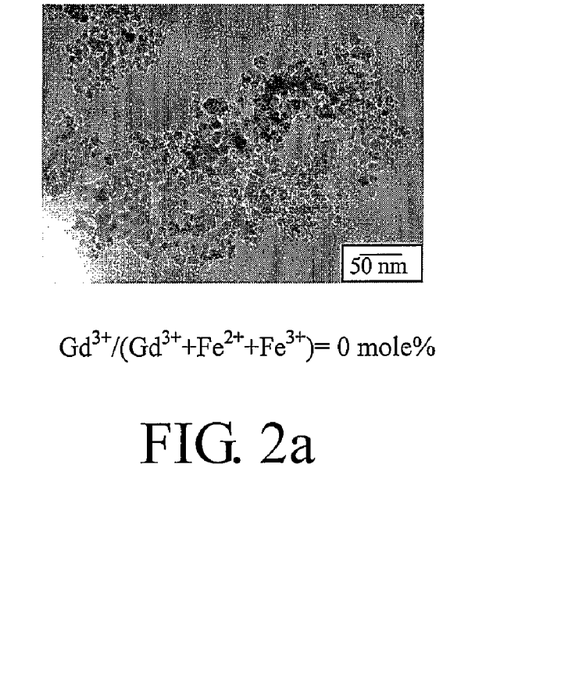
FIGS. 2a-2d show the magnetic nanoparticles in Example 1 by Transmission Electron Microscope (TEM) observation.
Figure 2B:
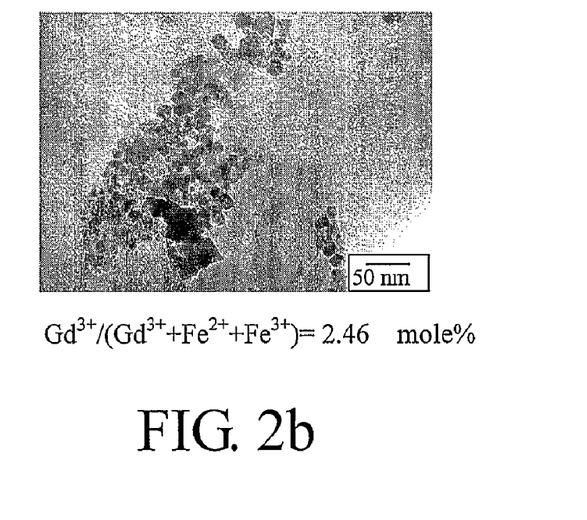
Figure 2C:
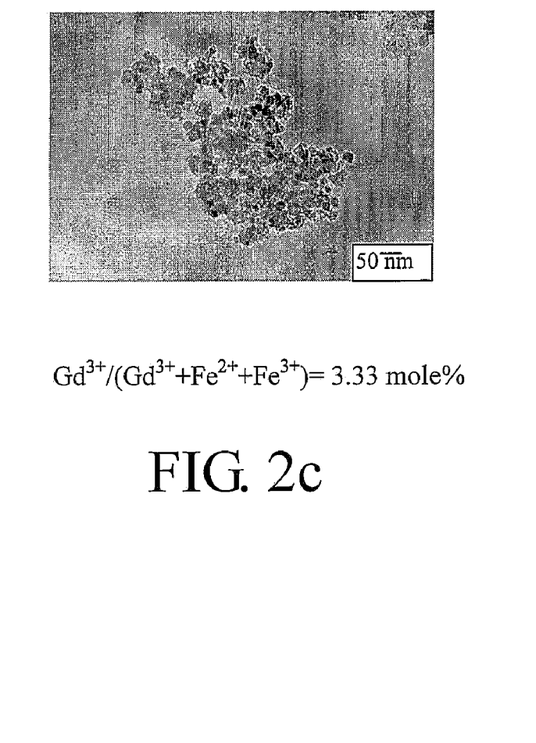
Figure 2D:
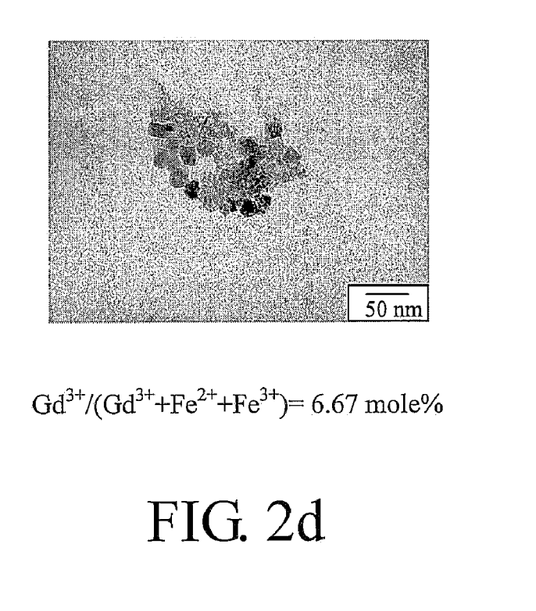
Figure 3:
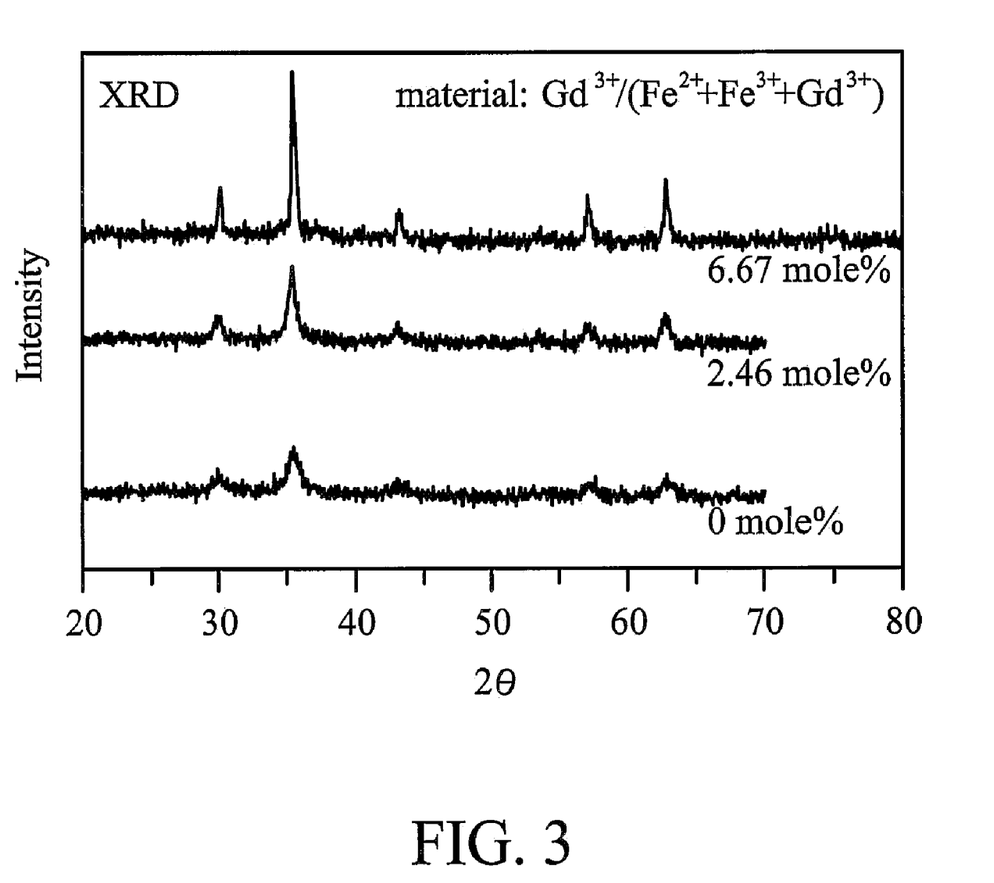
FIG. 3 shows the X-ray diffraction (XRD) analysis of the magnetic nanoparticles in Example 1.

FIG. 3 shows the XRD analysis of the magnetic nanoparticles in Example 1, further proving that the magnetic nanoparticles are iron oxide nanoparticles.

3. Inductively Coupled Plasma - Atomic Emission Spectrometry (ICP-AES)

Figure 4:
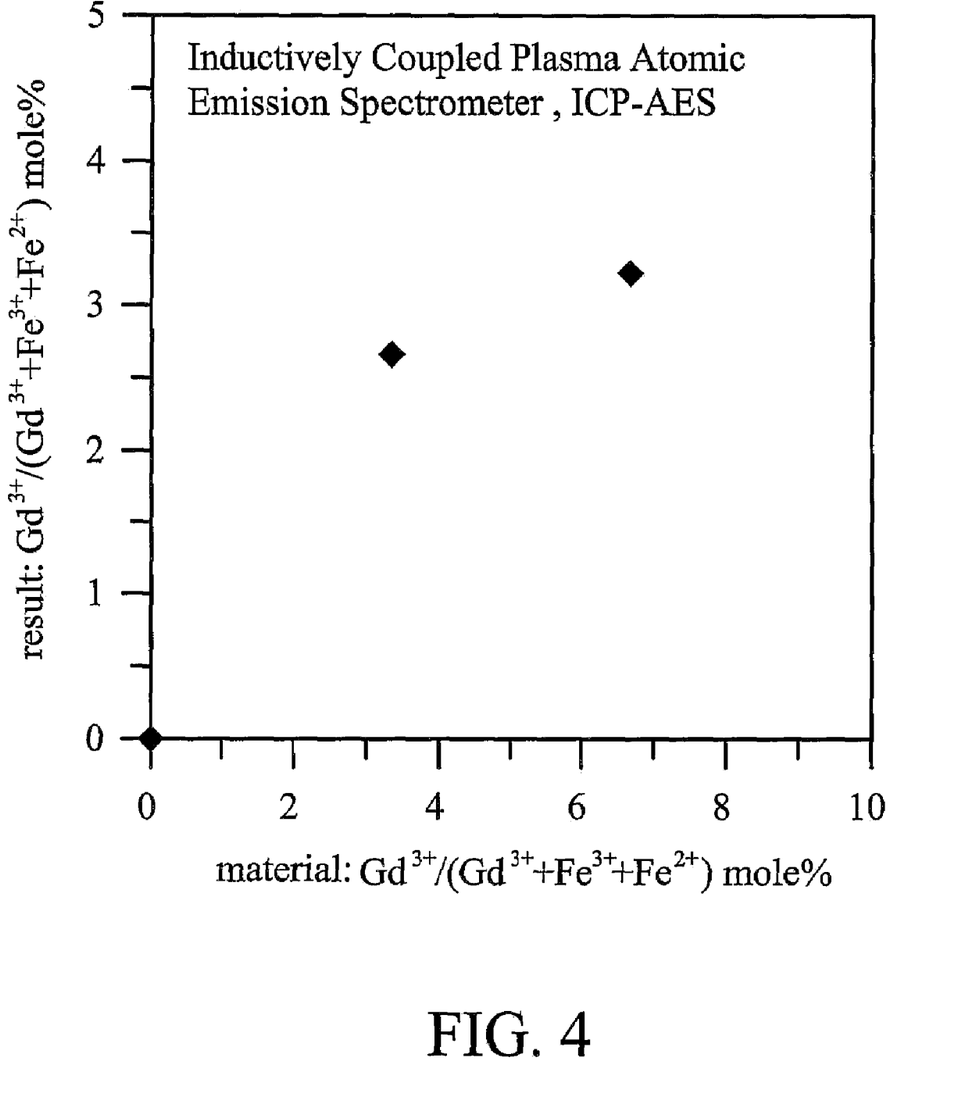
FIG. 4 shows the Inductively Coupled Plasma—Atomic Emission Spectrometry(ICP-AES) analysis of the magnetic nanoparticles in Example 1.

FIG. 4 shows the ICP-AES analysis of the magnetic nanoparticles in the embodiment. The magnetic nanoparticles with an initial $Gd^{3+}/(Gd^{3+}+Fe^{2+}+Fe^{3+})$ mixing ratio of 0 mol %, 3.33mol % or 6.67mol % have a final $Gd^{3+}/(Gd^{3+}+Fe^{2+}+Fe^{3+})$ ratio in the nanoparticles of 0 mol %, 2.65mol % or 3.20 mol %.

4. Super-conducting Quantum Interference Device (SQUID)

Figure 5:
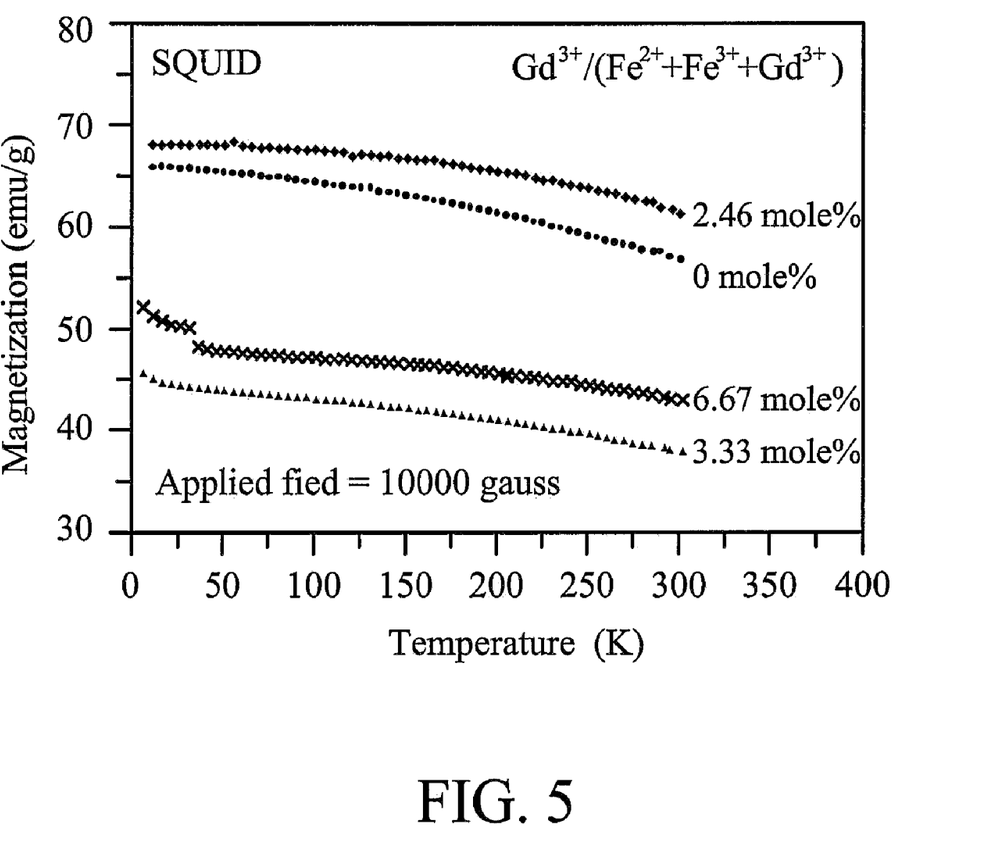
FIG. 5 shows the Super-conducting Quantum Interference Device (SQUID) analysis of the magnetic nanoparticles in Example 1.

FIG. 5 shows the SQUID analysis of the magnetic nanoparticles in the embodiment. The results indicate a 3-8% increased magnetization of the magnetic nanoparticles having 2.46 mol % of $GdCl_3$ added.

5. Magnetic Resonance Imaging (MRI)

Figure 6:
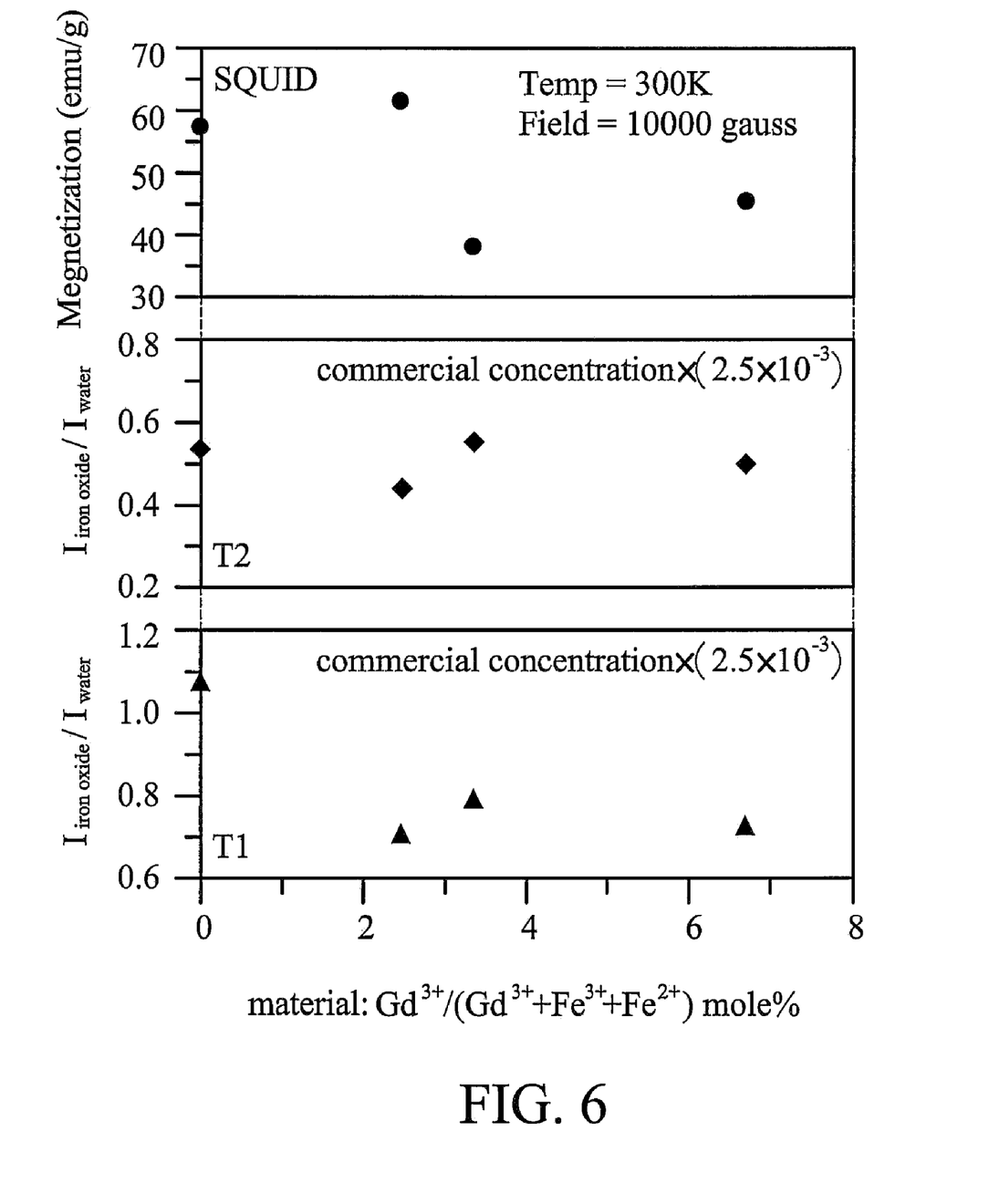
FIG. 6 shows the Magnetic Resonance Imaging (MRI) analysis of the magnetic nanoparticles in Example 1.

After clinically injecting a contrast agent, the concentration of the contrast agent is diluted by blood or body fluid, so the effective concentration is less than the concentration of the commercial contrast agent. Therefore, the provided magnetic nanoparticles were prepared as a contrast agent having a concentration $2.5 \times 10^{-3}$ times that of a commercial MRI iron oxide contrast agent. FIG. 6 shows the MRI analysis using the magnetic nanoparticles as contrast agent. The longitudinal coordinates represent the signal intensity ratios of the oxides and water molecules. The greater the coordinates deviates from 1, the better the contrast enhancement is. As shown in FIG. 6, all of the four kinds of magnetic nanoparticles with various $GdCl_3$ additive ratios exhibited contrast-enhancing capability. Especially, the iron oxide nanoparticles having 2.46 mol % additive $GdCl_3$ increased the contrast 18% more than that having non additive $GdCl_3$ under $T_2$-weighted conditions.

Accordingly, the Gd-including iron oxide nanoparticles enhance the contrast effectively and provide a clearer MRI image. Furthermore, the provided Gd-including iron oxide nanoparticles may be selectively modified by a molecule such as a liposome, polymer, aliphatic compound, or aromatic compound. The modified magnetic nanoparticle may further react with a substance having specificity, such as an antibody, a protein, a peptide, an enzyme, a carbohydrate, a glycoprotein, a nucleotide or a lipid to form a contrast agent having specificity.

EXAMPLE 2-1

In Examples 2-1 and 2-2, a magnetic nanoparticle comprising an iron oxide core and an inner-transition element shell. The iron oxide core is optionally substituted by a Gd complex, such as that described in Example 1. The inner-transition element of the shell and the core can be the same or different. The inner-transition element can be any of the lanthanides or the actinides, and the compound of the inner-transition element can be an oxide, sulfide, selenide, telluride, or polonide of the inner-transition element. In addition, a coupling agent between the core and the shell is further provided. The coupling agent has terminal functional groups, such as carboxyl group, amino group, or other suitable group. The surface of the shell can be further modified by liposome, polymer, aliphatic compound, aromatic compound or combinations thereof.

EXAMPLE 2-1

(Preparation of Gd-Iron Oide Core/Gd Complex Shell Nanoparticles)

In Example 2-1, Gd-iron oxide core/Gd complex shell nanoparticles were utilized in imaging, diagnosis, therapy, and biomaterial separation, such as an MRI contrast agent. First, $FeCl_3.6H_2O$ powders (0.02 mole) were dissolved in ethylene glycol (160 ml). $FeCl_3$ powders were replaced by $GdCl_3$ in various ratios, such as 0 mol % (no substitution), 3 mol %, or 5 mol %. Sodium acetate (14.4 g) was then added to the solution and stirred for 30 minutes. The mixture was charged in an autoclave and stirred at 800 rpm for 8 hours at 200□. The resulting particles were washed by Dl water and ethanol. 0.1 g of the washed particles is added to ethanol (22 g) and Dl water (4 g) for ultra-sonic vibration for 30 minutes to form the core. The mixture was added TEOS (0.168 mL) and APTES (0.044 mL) and stirred for 2 hours, thereby forming the coupling agent covering the core. The described particles (0.1 g) were added sodium borate buffer (2.6 mL), 1-methyl 2-pyrolidinone (7.4 mL), and succinic anhydride (2.4 g), and then stirred for 2 hours, such that the terminal amino group of the coupling agent was transferred to carboxyl group. These modified particles (0.3 g) were added to ethylene (30 mL) and Dl water (120 mL), and then ultrasonic vibrated for 30 minutes. The mixture is then added by $GdCl_3$ powder (0.13 g), $KNO_3$ (0.11 g), and hextamethylenetramine (2.0 g), and the temperature of the mixture was raised to and remained at 80° C. for 3 hours. The resulting particles were washed by Dl water.

Characterization of Gd-iron oxide core nanoparticles in Example 2-1

1. Scanning Electron Microscope (SEM)

Figure 7A:
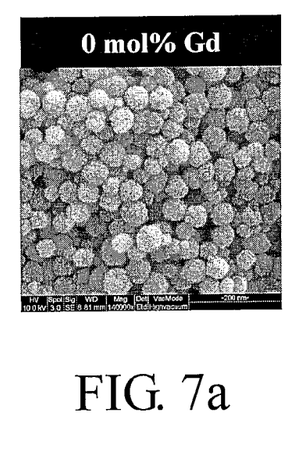
FIGS. 7a-7c show cores of the magnetic nanoparticles in Example 2-1 observed by Scanning Electron Microscope (SEM)
Figure 7B:
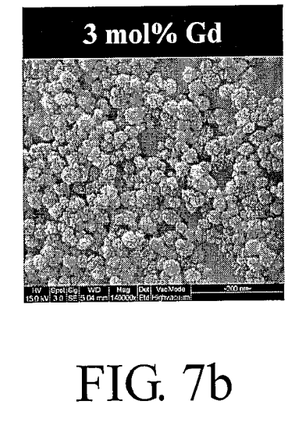
Figure 7C:
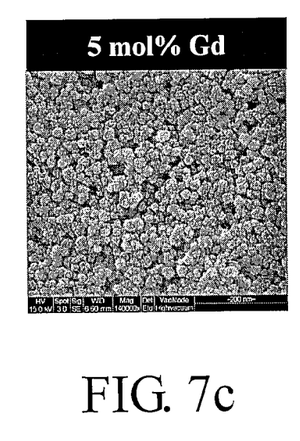

The magnetic nanoparticles were then observed by SEM. FIGS. 7a-7c respectively show the magnetic nanoparticles of $Gd^{3+}/(Gd^{3+}+Fe^{3+})$ at initial mixing ratios of 0, 3, and 5 mol %, with average diameters of about 159.3±28.3 nm, 95.6±18.9 nm, and 72.5±11.2 nm, respectively.

2. X-Ray Diffraction (XRD)

Figure 8A:
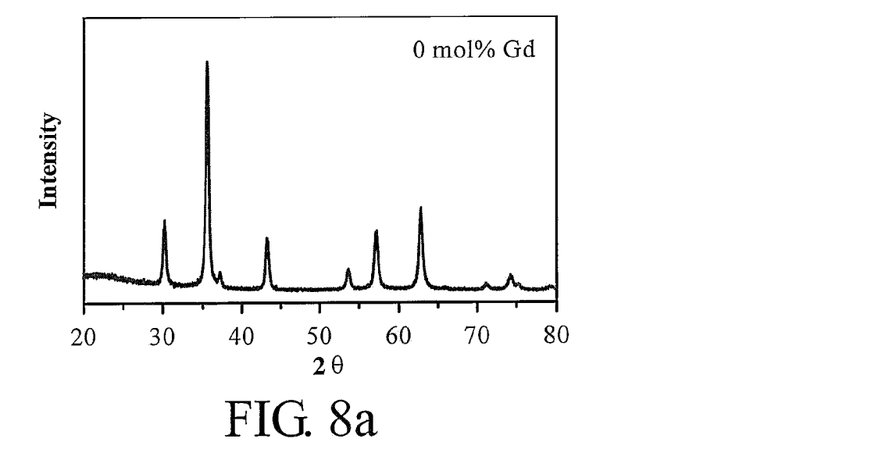
FIG. 8a-8c show the X-ray diffraction (XRD) analysis of the cores of the magnetic nanoparticles in Example 2-1.
Figure 8B:
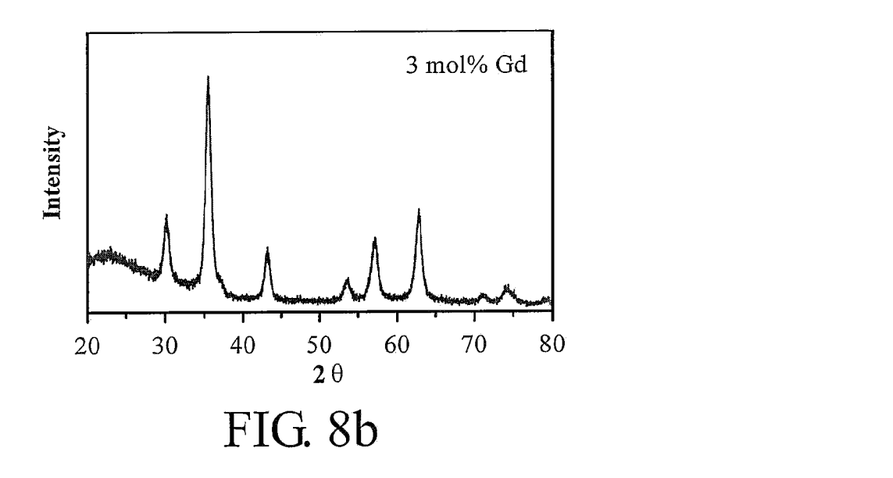
Figure 8C:
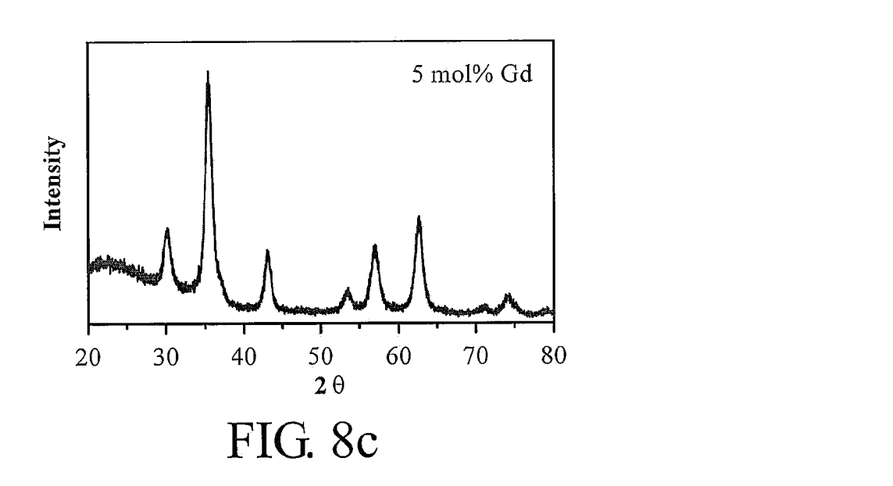

FIGS. 8a-8c show the XRD analysis of the magnetic nanoparticles in Example 2-1, and further prove that the core is substantially iron oxide.

3. Inductively Coupled Plasma—Atomic Emission Spectrometry (ICP-AES)

ICP-AES analysis shows that the magnetic nanoparticles with $Gd^{3+}/(Gd^{3+}+Fe^{3+})$ initial mixing ratios of 0 mol %, 3 mol %, and 5 mol % in core have a final $Gd^{3+}/(Gd^{3+}+Fe^{3+})$ ratio in the nanoparticles of 0 mol %, 1.4 mol %, and 2.1 mol % in core.

4. Nihydrin Test

Magnetic nanoparticles were tested by nihydrin. If the core surface is modified to carboxyl groups, the color of nihydrin test is not blue-purple. If the core surface is modified to amino groups, the color of nihydrin test is blue-purple. The nihydrin test shows that the core surface was modified to carboxyl groups before the shell was formed.

Characterization of Gd-Iron Oxide Core/Gd Complex Shell Nanoparticles in Example 2-1

1. Transmission Electron Microscope (TEM)

Figure 9A:
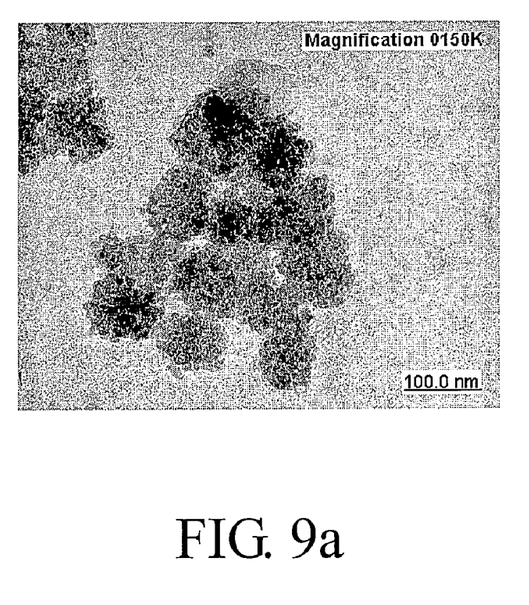
FIG. 9a-9b show the core/shell magnetic nanoparticles in Example 2-1 observed by Transmission Electron Microscope (TEM)
Figure 9B:
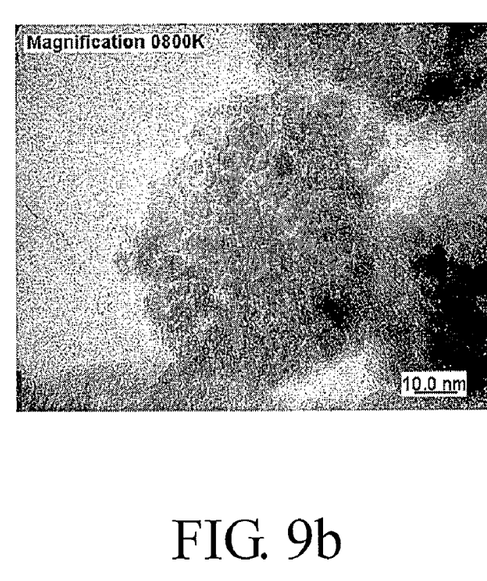

The magnetic nanoparticle core/shell structure was then observed by TEM, as shown in FIGS. 9a-9b.

2. EDS (energy-dispersive X-ray spectroscopy)

Figure 10A:
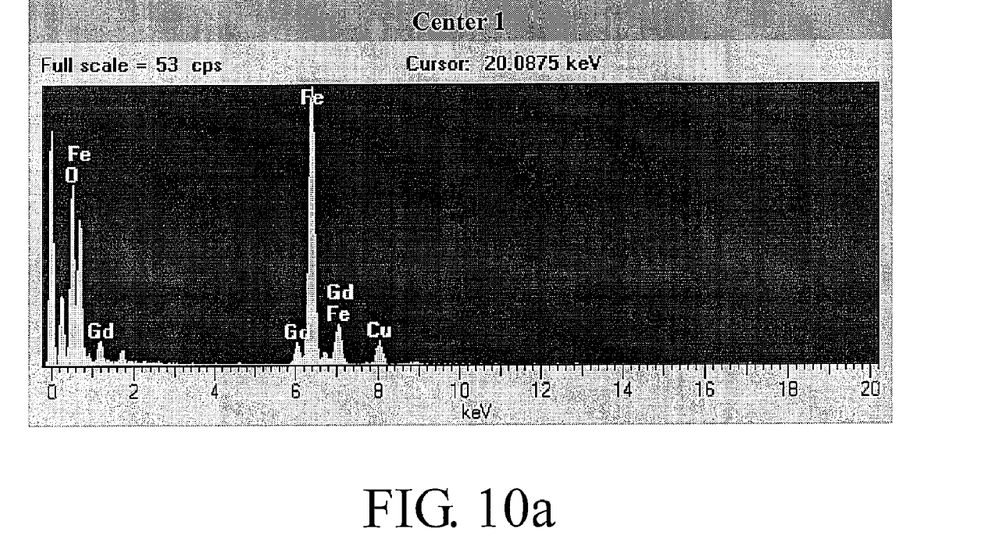
FIGS. 10a-10b show the Gd/(Gd+Fe) ratio of the center/edge of the core/shell magnetic nanoparticles in Example 2-1 observed by Energy-Dispersive X-ray Spectroscopy (EDS)
Figure 10B:
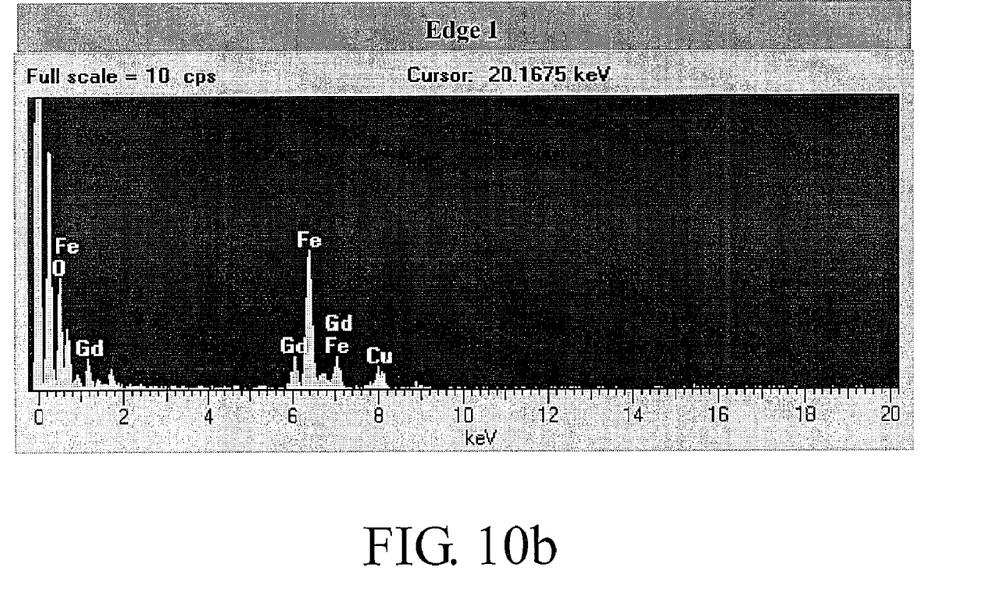

FIGS. 10a-10b show the EDS analysis of the core/shell magnetic nanoparticles in Example 2-1. In this example, the $Gd^{3+}/(Gd^{3+}+Fe^{3+})$ initial mixing ratio in core is 3 mol %. Magnetic nanoparticles were set on copper net for analysis, some copper signal was thus produced. The $Gd^{3+}/(Gd^{3+}+Fe^{3+})$ ratios of the center in nanoparticles were 6.81, 6.58, and 8.12 atomic %, averaged as 7.17±0.83 atomic %. The $Gd^{3+}/(Gd^{3+}+Fe^{3+})$ ratios of edge in nanoparticles were 19.25, 9.13, and 15.39 atonic %, averaged as 14.59±5.11 atonic %.

Example 2-2

(Preparation of Gd-including iron oxide core/Gd complex shell nanoparticles)

In Example 2-2, iron oxide core/Gd complex shell nanoparticles were utilized in imaging, diagnosis, therapy, and biomaterial separation, such as an MRI contrast agent. First, $FeCl_3.6H_2O$ powders (0.02 mole) was dissolved in ethylene glycol (160 ml). Sodium acetate (14.4 g) and carboxymethylcellulose sodium salt (4.0 g) were then added to the solution and stirred for 30 minutes. The mixture is charged in an autoclave for stirring at 800 rpm for 8 hours at 200□. The resulting particles, the iron oxide core covered by the coupling agent, were washed by Dl water and ethanol. These modified particles (0.3 g) were added to ethylene (30 mL) and Dl water (120 mL), and then subjected to ultrasonic vibration for 30 minutes. $GdCl_3$ powder (0.13 g), $KNO_3$ (0.11 g), and hextamethylenetramine (2.0 g) were then added to the mixture, and the temperature of the mixture was raised to and remained at 80° C. for 3 hours. The resulting particles were washed by Dl water.

Characterization of Gd-Iron Oxide Core/Gd Complex Shell Nanoparticles in Example 2-2

1. Scanning Electron Microscope (SEM)

Figure 11:
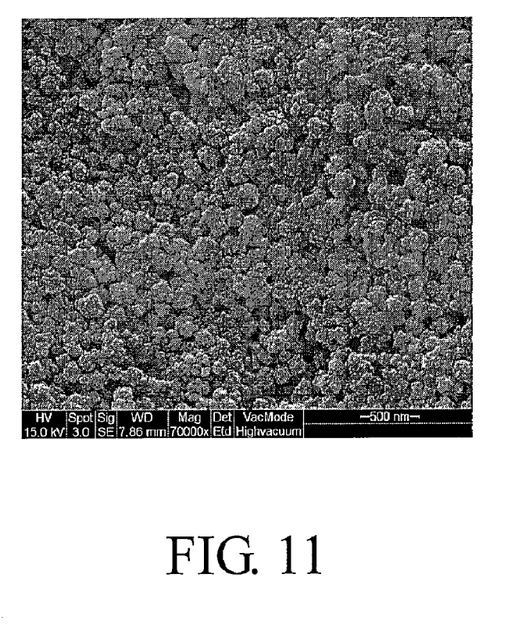
FIG. 11 shows the core/shell magnetic nanoparticles in Example 2-2 observed by Scanning Electron Microscope (SEM)

The magnetic nanoparticles were then observed by SEM as shown in FIG. 11.

2. Transmission Electron Microscope (TEM)

Figure 12:
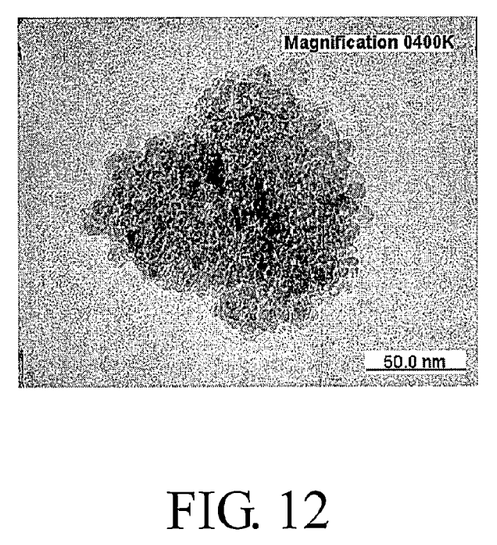
FIG. 12 shows the core/shell magnetic nanoparticles in Example 2-2 by Transmission Electron Microscope (TEM) observation.

The magnetic nanoparticle core/shell structure was then observed by TEM, as shown in FIG. 12.

3. EDS (energy-dispersive X-ray spectroscopy)

Figure 13A:
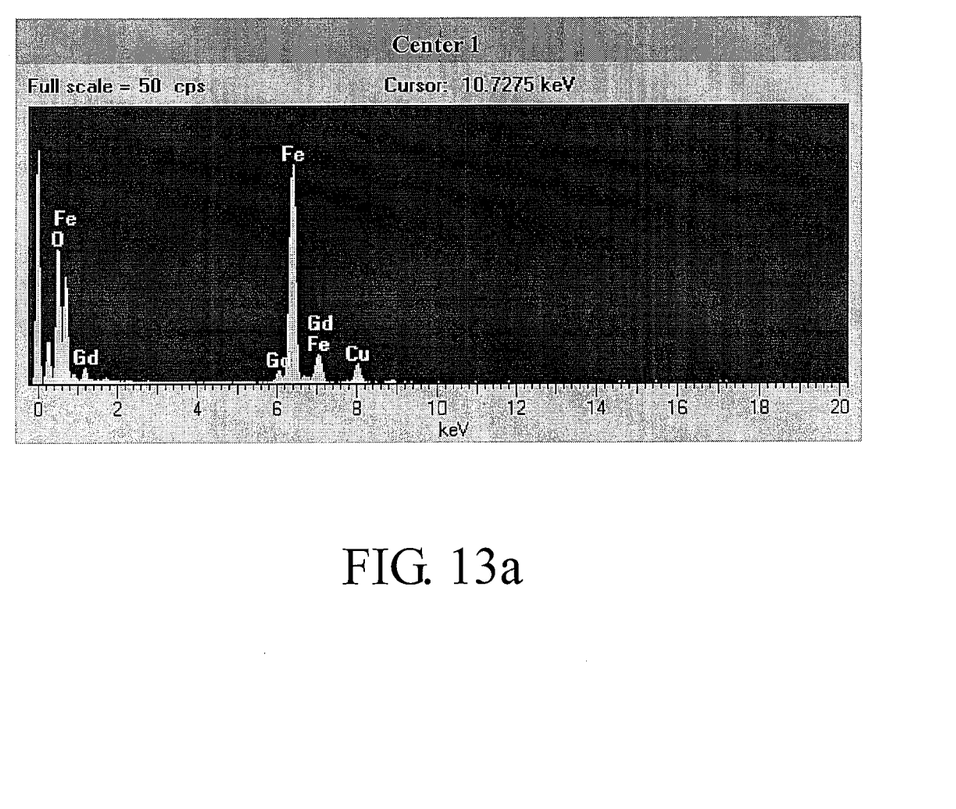
FIGS. 13a-13b show the Gd/(Gd+Fe) ratio of center/edge of the core/shell magnetic nanoparticles in Example 2-2 observed by Energy-Dispersive X-ray Spectroscopy (EDS).
Figure 13B:
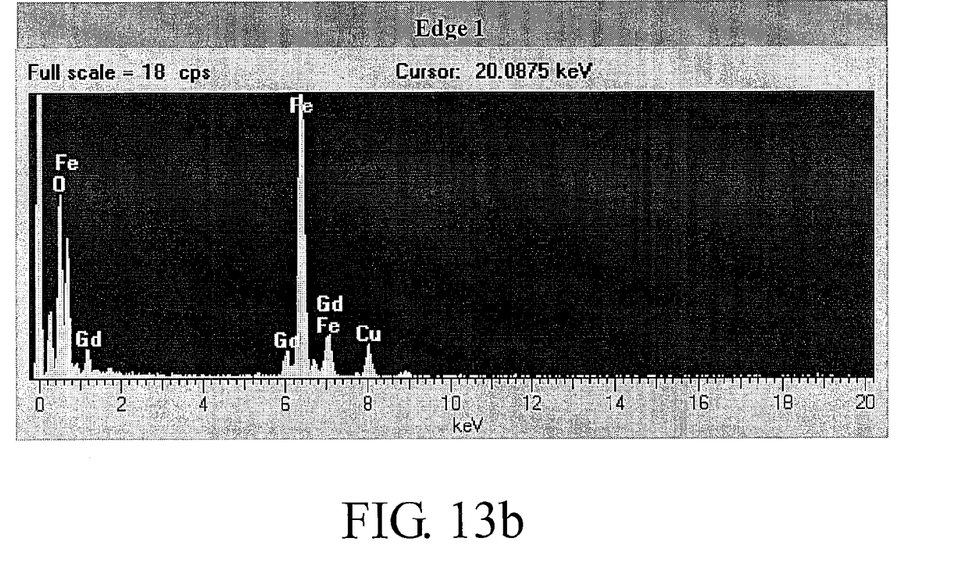

FIGS. 13a-13b show the EDS analysis of the core/shell magnetic nanoparticles in Example 2-2. Magnetic nanoparticles were set on copper net for analysis; some copper signal was thus produced. The $Gd^{3+}/(Gd^{3+}+Fe^{3+})$ ratios of center in nanoparticles were 5.29, 4.75, and 4.76 atonic %, averaged as 4.93±0.31 atonic %. The $Gd^{3+}/(Gd^{3+}+Fe^{3+})$ ratios of edge in nanoparticles were 8.06, 6.67, and 7.65 atonic %, averaged as 7.46±0.71 atonic %.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A magnetic nanoparticle comprising:
    a core represented as $Fe_xM^a{}_vZ_y$, wherein $M^a$ is an inner-transition element, Z is oxygen, x is greater or equal to 0, and v, y are positive numbers; and
    a shell of an inner-transition element $M^b$ or the compound thereof.

2. The magnetic nanoparticle as claimed in claim 1, wherein the inner-transition elements $M^a$ and $M^b$ are selected from the lanthaniides or the actinides.

3. The magnetic nanoparticle as claimed in claim 1, wherein the inner-transition elements $M^a$ and $M^b$ are the same element.

4. The magnetic nanoparticle as claimed in claim 1, wherein the inner-transition elements $M^a$ and $M^b$ are different elements.

5. The magnetic nanoparticle as claimed in claim 1, wherein the compound of the inner-transition element $M^b$ is a complex.

6. The magnetic nanoparticle as claimed in claim 1, wherein the magnetic nanoparticle is applicable in imaging, diagnosis, therapy and biomaterial separation.

7. The magnetic nanoparticle as claimed in claim 1, further modified by at least one molecule.

8. The magnetic nanoparticle as claimed in claim 7, wherein the molecule is a liposome, polymer, aliphatic compound, aromatic compound or combinations thereof.

9. The magnetic nanoparticle as claimed in claim 7, wherein the magnetic nanoparticle further reacts with at least one substance having specificity.

10. The magnetic nanoparticle as claimed in claim 9, wherein the substance having specificity is an antibody, a protein, a peptide, an enzyme, a carbohydrate, a glycoprotein, a nucleotide or a lipid.

11. The magnetic nanoparticle as claimed in claim 1, wherein the magnetic nanoparticle further reacts with at least one substance having specificity.

12. The magnetic nanoparticle as claimed in claim 11, wherein the substance having specificity is an antibody, a protein, a peptide, an enzyme, a carbohydrate, a glycoprotein, a nucleotide or a lipid.

13. The magnetic nanoparticle as claimed in claim 1, further comprising a coupling agent between the core and the shell.

14. The magnetic nanoparticle as claimed in claim 13, wherein the coupling agent has terminal functional groups comprising carboxyl group or amino group.

15. A magnetic nanoparticle applicable in imaging, diagnosis, therapy and biomaterial separation, comprising:
    a core represented as $Fe_xM^a{}_vZ_y$, wherein Ma is an inner-transition element, Z is oxygen, x is greater or equal to 0, and v, y are positive numbers; and
    a shell of an inner-transition element Mb or the compound thereof.

16. The magnetic nanoparticle as claimed in claim 15, wherein the inner-transition elements $M^a$ and $M^b$ are selected from the lanthanides or the actinides.

17. The magnetic nanoparticle as claimed in claim 15, wherein the inner-transition elements $M^a$ and $M^b$ are the same element.

18. The magnetic nanoparticle as claimed in claim 15, wherein the inner-transition elements $M^a$ and $M^b$ are different elements.

19. The magnetic nanoparticle as claimed in claim 15, wherein the compound of the inner-transition element $M^b$ is a complex.

20. The magnetic nanoparticle as claimed in claim 15, further modified by at least one molecule.

21. The magnetic nanoparticle as claimed in claim 20, wherein the molecule is a liposome, polymer, aliphatic compound, aromatic compound or combinations thereof.

22. The magnetic nanoparticle as claimed in claim 20, wherein the magnetic nanoparticle further reacts with at least one substance having specificity.

23. The magnetic nanoparticle as claimed in claim 22, wherein the substance having specificity is an antibody, a protein, a peptide, an enzyme, a carbohydrate, a glycoprotein, a nucleotide or a lipid.

24. The magnetic nanoparticle as claimed in claim 15, wherein the magnetic nanoparticle further reacts with at least one substance having specificity.

25. The magnetic nanoparticle as claimed in claim 24, wherein the substance having specificity is an antibody, a protein, a peptide, an enzyme, a carbohydrate, a glycoprotein, a nucleotide or a lipid.

26. The magnetic nanoparticle as claimed in claim 15, further comprising a coupling agent between the core and the shell.

27. The magnetic nanoparticle as claimed in claim 26, wherein the coupling agent has terminal functional groups comprising carboxyl group or amino group.

* * * * *